United States Patent
Sartor et al.

(10) Patent No.: US 9,668,763 B2
(45) Date of Patent: Jun. 6, 2017

(54) SYSTEM FOR MYOMECTOMY AND MORCELLATION

(71) Applicant: COVIDIEN LP, Mansfield, MA (US)

(72) Inventors: Joe D. Sartor, Longmont, CO (US); David N. Heard, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 359 days.

(21) Appl. No.: 14/303,242

(22) Filed: Jun. 12, 2014

(65) Prior Publication Data
US 2015/0073429 A1    Mar. 12, 2015

Related U.S. Application Data

(60) Provisional application No. 61/876,434, filed on Sep. 11, 2013, provisional application No. 61/876,420, filed on Sep. 11, 2013.

(51) Int. Cl.
| | |
|---|---|
| *A61B 17/32* | (2006.01) |
| *A61B 17/02* | (2006.01) |
| A61B 17/34 | (2006.01) |
| A61B 17/00 | (2006.01) |
| A61B 17/22 | (2006.01) |
| A61B 17/42 | (2006.01) |

(52) U.S. Cl.
CPC .... *A61B 17/32002* (2013.01); *A61B 17/0218* (2013.01); *A61B 17/3423* (2013.01); *A61B 2017/003* (2013.01); *A61B 2017/00017* (2013.01); *A61B 2017/00314* (2013.01); *A61B 2017/00349* (2013.01); *A61B 2017/22044* (2013.01); *A61B 2017/320024* (2013.01); *A61B 2017/3445* (2013.01); *A61B 2017/3488* (2013.01); *A61B 2017/4216* (2013.01)

(58) Field of Classification Search
CPC ............ A61B 2017/320024; A61B 2017/4216
See application file for complete search history.

(56) References Cited

U.S. PATENT DOCUMENTS

| | | | |
|---|---|---|---|
| 5,520,634 A | 5/1996 | Fox et al. | |
| 6,039,748 A | 3/2000 | Savage et al. | |
| 6,165,188 A * | 12/2000 | Saadat | A61B 17/3207 604/22 |
| 6,468,228 B1 | 10/2002 | Topel et al. | |

(Continued)

FOREIGN PATENT DOCUMENTS

WO    2009/039506 A1    3/2009

OTHER PUBLICATIONS

U.S. Appl. No. 14/303,366, filed Jun. 12, 2014, Inventor: Sartor et al.

*Primary Examiner* — Gregory Anderson

(57) ABSTRACT

Surgical instruments and surgical systems including the surgical instrument and a morcellator. The surgical instrument includes a tool assembly having an articulating joint and a screw positioned at a distal end of the articulating joint. The articulating joint is configured to articulate a distal portion of the tool assembly at an angle in relation to the longitudinal axis of the surgical instrument. The screw is configured to engage tissue, for example, a myoma in the uterine wall of a patient, and is configured to pitch and roll the tissue to expose cutting planes. The morcellator is configured to engage the tissue to morcellate the tissue and remove the tissue from a patient.

9 Claims, 10 Drawing Sheets

(56) References Cited

U.S. PATENT DOCUMENTS

| | | | |
|---|---|---|---|
| 6,821,285 B2 * | 11/2004 | Laufer | A61B 17/0401 606/151 |
| 7,033,357 B2 | 4/2006 | Baxter et al. | |
| 7,918,795 B2 | 4/2011 | Grossman | |
| 8,308,746 B2 | 11/2012 | Pravong et al. | |
| 2007/0225745 A1 | 9/2007 | Arnal et al. | |
| 2008/0039883 A1 | 2/2008 | Nohilly | |
| 2008/0269772 A1 | 10/2008 | Choi | |
| 2011/0121049 A1 | 5/2011 | Malinouskas et al. | |
| 2012/0316572 A1 | 12/2012 | Rosenblatt et al. | |
| 2013/0123797 A1 | 5/2013 | Livneh | |
| 2014/0257112 A1 * | 9/2014 | Siegel | A61B 18/1485 600/471 |

* cited by examiner though which were filed on Sep. 11, 2013This application is related to U.S. patent application Ser. No. 14/303366, filed on Jun. 12, 2014. The entire contents of each of the above applications are hereby incorporated herein by reference.

SYSTEM FOR MYOMECTOMY AND MORCELLATION

CROSS-REFERENCE TO RELATED APPLICATIONS

This application claims the benefit of, and priority to, U.S. Provisional Patent Application Nos. 61/876,434 and 61/876,420, both of which were filed on Sep. 11, 2013This application is related to U.S. patent application Ser. No. 14/303366, filed on Jun. 12, 2014. The entire contents of each of the above applications are hereby incorporated herein by reference.

BACKGROUND

1. Technical Field

The present disclosure relates generally to surgery. More particularly, the present disclosure relates to methods, devices, and systems for locating and treating uterine fibroids.

2. Discussion of Related Art

Fibroids are benign tumors of the uterine myometria (i.e., muscle) and are the most common tumor of the female pelvis. Fibroid tumors affect up to 30% of women of childbearing age and can cause significant symptoms such as discomfort, pelvic pain, mennorhagia, pressure, anemia, compression, infertility, and miscarriage. Fibroids may be located in the myometrium, adjacent to the endometrium (i.e., submucosal), or in the outer layer of the uterus (i.e., subserosal). Most commonly, fibroids are a smooth muscle overgrowth that arise within the walls of the myometrium and can grow to be several centimeters in diameter.

Current treatment for fibroids includes medical treatment with non-steroidal anti-inflammatory drugs (NSAIDS), estrogen-progesterone combinations, and gonadotropin-releasing hormone analogues (GnRH analogues). Pharmacologic therapy with GnRH analogues is limited due to its side effects, such as hot flashes, vaginal dryness, mood changes, and bone density loss. Further, its relatively short time of treatment (e.g., about 3 months) offers temporary shrinkage, wherein the fibroids may regrow after medical discontinuation.

Hysterectomy (i.e., surgical removal of the uterus) is a common treatment for fibroids. It is performed up to 600,000 times annually in the United States. Indeed, fibroids are the indication for hysterectomy in up to one third of all cases. Hysterectomy for treating fibroids is generally effective but has many undesirable side effects such as loss of fertility, open surgery, sexual dysfunction, and long recovery time. There is also significant morbidity (e.g., sepsis, hemorrhage, peritonitis, bowel, and bladder injury), mortality, and costs associated with hysterectomy treatments.

Surgical myomectomy may be an open or laparoscopic surgical procedure to spare the tissue of the uterus. As an open procedure, myomectomy requires a laparotomy and a large incision to provide a surgeon with access to the fibroids to be removed.

Laparoscopic myomectomy remains technically challenging. A surgeon must access the uterus through a small incision and dissect the fibroid from the uterine wall with limited access and with limited directions of traction. Moreover, once the fibroid is dissected from the uterine wall the fibroid must be morcellated to remove it through the incision.

SUMMARY

A surgical system provided in accordance with the present disclosure includes a myomectomy screw retractor having an elongated body and a tool assembly. The elongated body defines a longitudinal axis. The tool assembly is disposed at a distal end of the elongated body and includes a screw and an articulating joint interconnection the elongated body and the screw. The articulating joint is articulatable to move the tool assembly between a linear condition and an articulated condition. The articulating joint operatively associated with a first actuator. The screw selectively coupled to a rotating shaft extending proximally from the screw through the elongated body. The screw disposed along the longitudinal axis when the tool assembly is in the linear condition and the screw defining an angle θ with respect to the longitudinal axis when the tool assembly is in the articulated condition.

The tool assembly can further include a guide wire coaxially disposed within the screw and having a retracted position and an extended position. A distal end of the guide wire is positioned proximally to a distal end of the screw in the retracted position; and is positioned distally of the distal end of the screw in the extended position. The guide wire can be operatively associated with a second actuator to move the guide wire between the retracted position and the extended position. The guide wire can also be removable through a proximal end of the elongated body. The tool assembly can also include a locking mechanism extendable about the outer surface of the screw.

In embodiments, the proximal end of the elongated body includes an adaptor including an interface for manipulating the tool assembly.

In some embodiments, the surgical system further includes a morcellator having an elongated tube and a cutting tube. The elongated tube includes a sleeve at the distal end of the elongated tube that defines a second longitudinal axis. The cutting tube is disposed within the sleeve. The cutting tube is activatable to rotate about the second longitudinal axis. As can be appreciated, the tube may be round as necessitated for a rotational morcellating blade but other energy modalities such as oscillation or radiofrequency electrosurgery support alternate tubes which may be shaped or designed in a manner to cause it to skive along the surface rather than plunge directly through tissue. The distal end of the cutting tube is positioned near the distal end of the sleeve. The morcellator can also include a motion detector positioned near the distal end of the elongated tube. The motion detector is configured to deactivate the cutting tube when the distal end of the elongated tube is displaced while the cutting tube is rotating.

In certain embodiments, the screw of the myomectomy screw retractor is operatively associated with a screw synchronizer configured to control the rotation of the rotating shaft and the morcellator includes a morcellator synchronizer operatively associated with the cutting tube. The screw synchronizer and the morcellator synchronizer are in communication to rotate the screw in cooperation with the rotation of the cutting tube.

In particular embodiments, the myomectomy screw retractor and/or the morcellator are end effectors configured to couple to powered surgical instruments and/or robotic surgical systems.

Also provided in accordance with the present disclosure is a method for dissecting a myoma from a uterine wall. The method includes inserting a myomectomy screw retractor, articulating a tool assembly of the myomectomy screw retractor, rotating the screw of the tool assembly, manipulating the myoma, and dissecting the myoma from the uterine wall. Inserting includes inserting a myomectomy screw retractor into a surgical site. Articulating includes articulating a tool assembly positioned at a distal end of the myomectomy screw retractor relative to the myomectomy screw retractor such that a screw of the tool assembly is positioned adjacent to the myoma orthogonal to the uterine wall. Rotating includes rotating the screw of the tool assembly into the myoma until the screw is substantially engaged with the myoma. Manipulating includes manipulating the myoma by pitching, rotating, and/or providing traction to the myoma to expose cutting planes. Dissecting includes dissecting the myoma from the uterine wall by cutting along the exposed cutting planes.

The method may further include extending a guide wire from the distal end of the screw into the myoma before rotating the screw. The myomectomy screw retractor can be coupled at a proximal end to a powered surgical instrument or to a robotic surgical system for inserting, articulating, manipulating, dissecting etc.

The method may further include providing a morcellator defining a second longitudinal axis, engaging the myoma with a morcellator, and activating the morcellator. Engaging includes engaging the outer surface of the myoma with a cutting tube disposed coaxially within a sheath at distal end of an elongated tube of the morcellator such that the myoma is positioned about the screw with the screw positioned perpendicular to the second longitudinal axis. Activating includes activating the cutting tube such that the cutting tube rotates about the second longitudinal axis to morcellate the myoma by drawing a strip of tissue from the outer surface of the myoma.

Further, to the extent consistent, any of the aspects and features described herein may be used in conjunction with any or all of the other aspects described herein.

BRIEF DESCRIPTION OF THE DRAWINGS

Various aspects of the present disclosure are described hereinbelow with reference to the drawings, wherein:

FIG. 2A is a side view of the tool assembly of a myomectomy screw retractor in accordance with the present disclosure including a flexible sheath;

DETAILED DESCRIPTION

Figure 1:
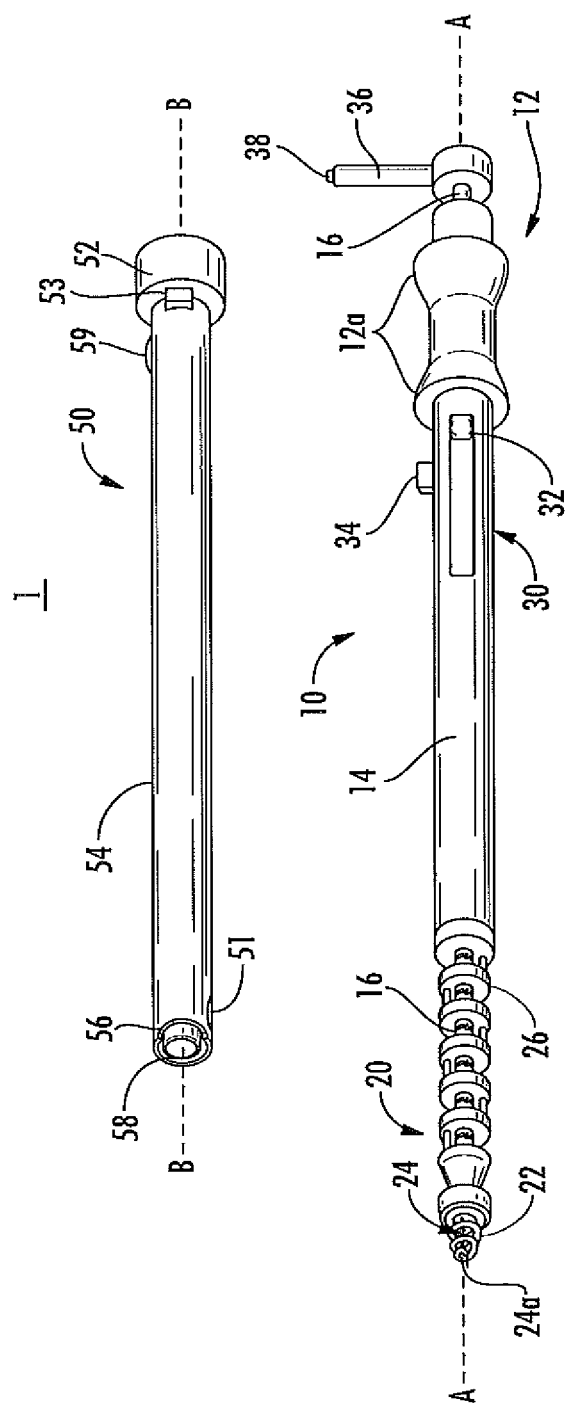
FIG. 1 is a perspective view of system for performing myomectomies in accordance with the present disclosure including a morcellator and a myomectomy screw retractor.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closest to the clinician and the term "distal" will refer to the portion of the device or component thereof that is furthest from the clinician. Throughout this description, the term "myoma" will refer to fibroids disposed on and/or within the walls of the uterus including leiomyoma masses, myoma masses, and other masses disposed on and/or within the walls of other organs of the body.

Referring now to FIG. 1, a surgical system 1 is provided in accordance with the present disclosure incorporating a myomectomy screw retractor 10 and a morcellator 50. The myomectomy screw retractor 10 includes a handle assembly 12, an elongated body 14 extending distally from the handle assembly 12 defining a longitudinal axis "A-A", and a tool assembly 20 positioned at a distal end of the elongated body 14. The handle assembly 12 includes an actuation assembly 30 having a first actuator 32, a second actuator 34, and a rotatable handle 36. The handle assembly 12 can also include a hand grip 12a. A rotatable shaft 16 is operably associated with rotatable handle 36 and extends through tool assembly 20 as described in detail below.

Figure 2:
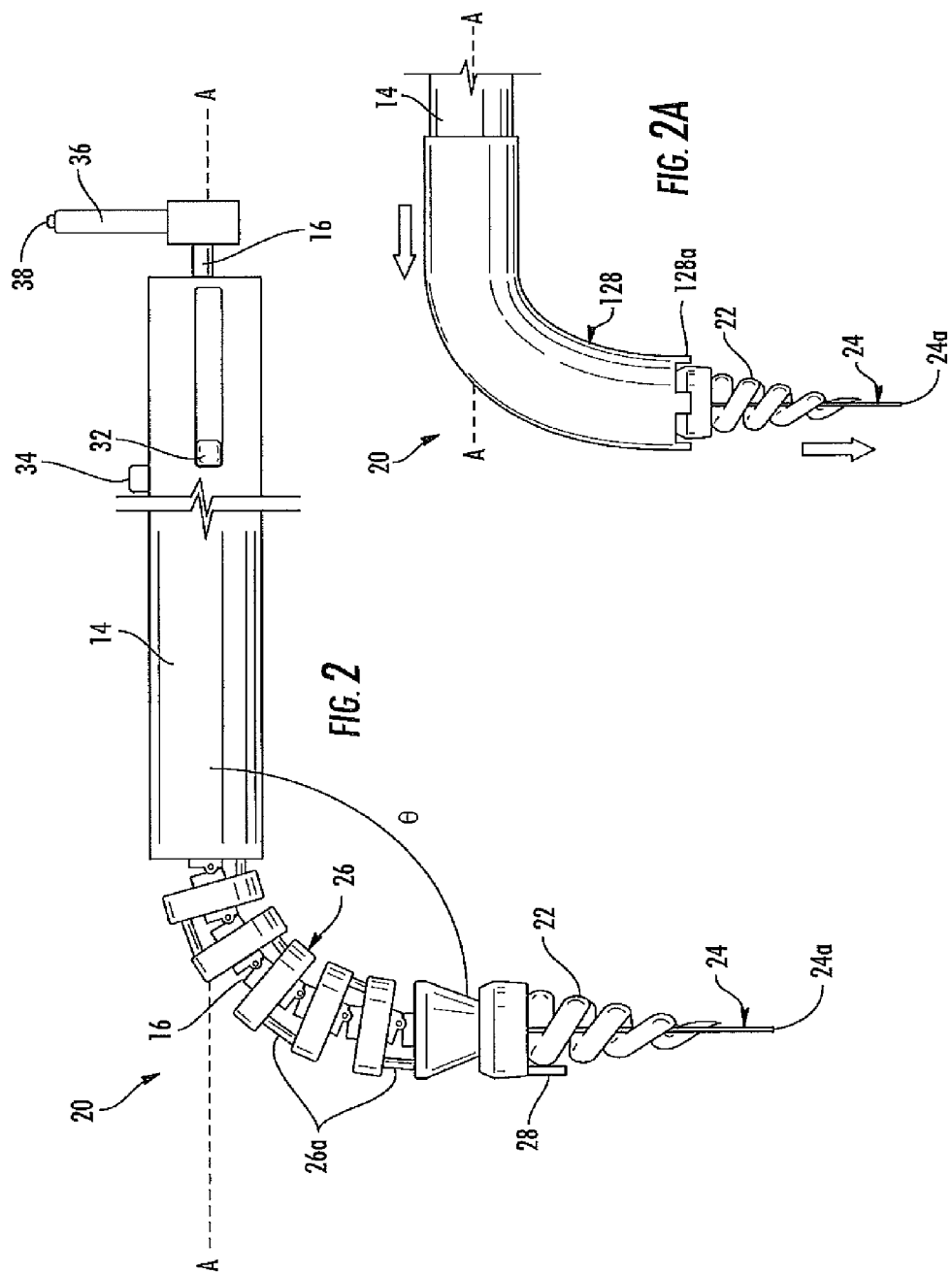
FIG. 2 is a side view of the myomectomy screw retractor of FIG. 1 in an articulated condition.

With additional reference to FIG. 2, tool assembly 20 includes a screw 22, a guide wire 24, and an articulating joint 26. Screw 22 is positioned distal to articulating joint 26 and is operatively associated with rotatable shaft 16. In embodiments, screw 22 is selectively couplable with and decouplable from rotatable shaft 16 to achieve a coupled condition, wherein screw 22 cooperates with the rotation of rotatable shaft 16, and a decoupled condition, wherein screw 22 is free to rotate independent of rotatable shaft 16. A coupling switch or button 38 transitions screw 22 between the coupled condition and the decoupled condition. In embodiments, coupling switch 38 is positioned on rotatable handle 36.

Guide wire 24 is coaxially disposed within screw 22 and has a retracted position (FIG. 1) and an extended position (FIG. 2). In the retracted position, distal end 24a of guide wire 24 is proximal to the distal end of screw 22. In the extended position, distal end 24a of guide wire 24 extends from the distal end of screw 22. A distal end 24a of guide wire 24 is configured to pierce tissue and can be sharpened. A proximal portion of guide wire 24 extends through rotatable shaft 16 and is operatively associated with second actuator 34. Second actuator 34 transitions guide wire 24 between the retracted position and the extended position. In some embodiments, guide wire 24 is completely removable from the proximal end of myomectomy screw retractor 10.

Tool assembly 20 can include a locking mechanism 28 configured to lock the rotation of a myoma relative to screw 22. In embodiments, locking mechanism 28 is a flat strip that protrudes distally near the outer circumference of screw 22. In some embodiments, locking mechanism 28 is a flat strip, which protrudes through screw 22 or from the distal end of screw 22. The strip, in some embodiments, may be at least partially flexible.

Referring to FIG. 2A, tool assembly 20 includes a locking mechanism or flexible sheath 128 configured lock the rotation of a myoma relative to screw 22. Flexible sheath 128 can include teeth 28a configured to engage the myoma.

Referring again to FIGS. 1 and 2, tool assembly 20 has a linear condition (FIG. 1), wherein articulating joint 26 is positioned along longitudinal axis "A-A", and an articulated condition (FIG. 2), wherein articulating joint 26 displaces screw 22 at an angle θ relative to longitudinal axis "A-A". Articulating joint 26 is operatively associated with first actuator 32 to transition tool assembly 20 between the linear condition and the articulated condition. In embodiments, articulating joint 26 includes linkages 26a operatively associated with first actuator 32.

Referring back to FIG. 1, morcellator 50 includes a handle 52, an elongated tube 54, a sleeve 56, a cutting tube 58, and an activation button 59. Elongated tube 54 extends distally from handle and defines a longitudinal axis "B-B". Cutting tube 58 is disposed coaxially within a distal portion of elongated tube 54. Sleeve 56 is positioned coaxial over cutting tube 58 at the distal end of elongated tube 54 and extends over the distal end of cutting tube 58 such that cutting tube is prevented from plunging or coring target tissue, as described in detail below. In embodiments, morcellator 50 includes a motion detector 51 such as a multiaxis accelerometer. The motion detector 51 can be positioned on sleeve 56 and/or on the distal portion of elongated tube 54.

Referring now to FIGS. 3-10, surgical system 1 is shown and described in use to dissect and morcellate a myoma from a uterus in accordance with the present disclosure. Elongated body 14 of myomectomy screw retractor 10 is inserted into a surgical site of a patient to access a uterus 90 of the patient. The surgical site can be an incision 81 or a natural orifice of the body. In embodiments, an access device 82 is inserted into the surgical site to provide resealable access to the surgical site. The elongated body 14 being inserted through a port of access device 82. In alternative embodiments, elongated body 14 is inserted directly through incision 81. Elongated body 14 may have a diameter of approximately 5 mm to approximately 8 mm; however, larger and smaller diameters are also envisioned. It will be appreciated that additional instruments such as an obturator (not shown), a camera (not shown), a light source 89, a cutting instrument (not shown), and/or morcellator 50 may be inserted through tissue layer 80 of the patient through incision 81 and/or a second incision 81a. These additional instruments can be used to visualize the operation of myomectomy screw retractor 10 and manipulate and/or dissect tissue within body cavity 80a.

Figure 3:
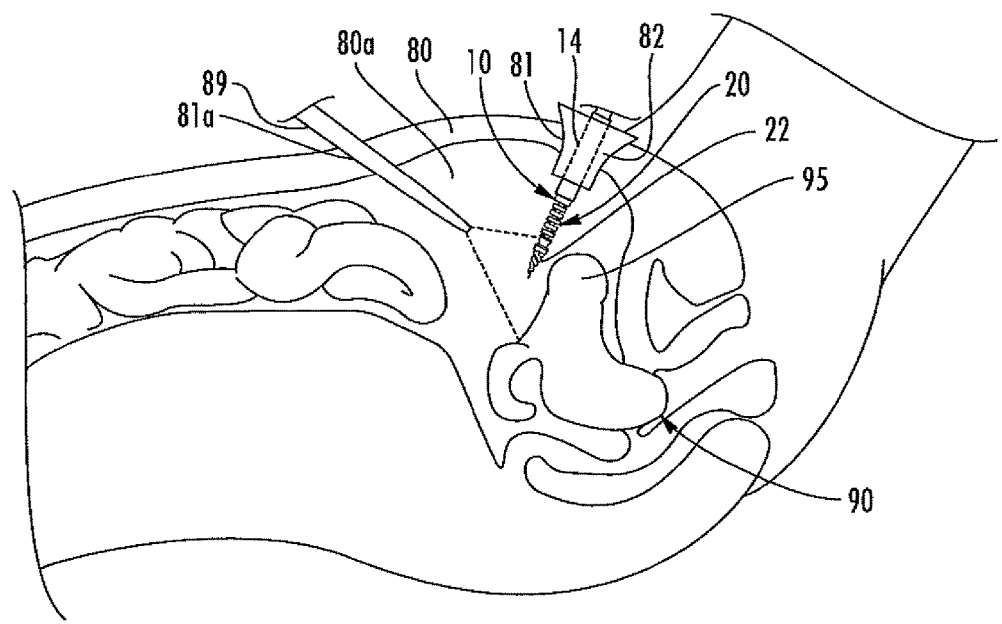
FIG. 3 is a perspective view of a myomectomy screw retractor in accordance with the present disclosure inserted into the abdominal cavity of a patient.

Referring to FIG. 3, when myomectomy screw retractor 10 is inserted into body cavity 80a, tool assembly 20 is in the linear condition to facilitate insertion of myomectomy screw retractor 10 through access port 82 and guide wire 24 is in the retracted position.

Figure 4:
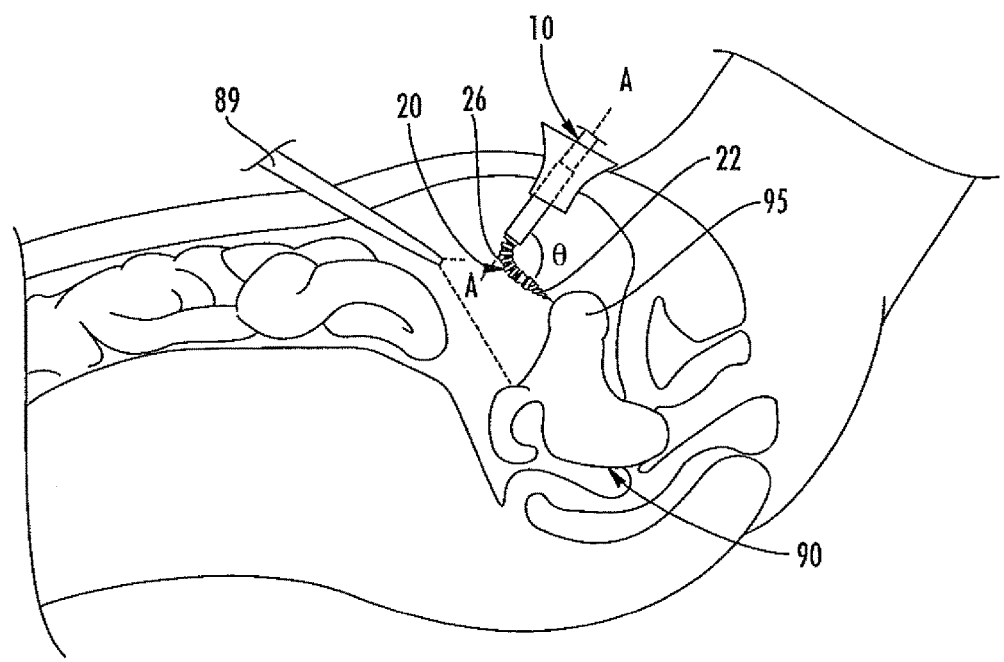
FIG. 4 is a perspective view of the myomectomy screw retractor of FIG. 3 in an articulated condition positioned over a myoma.

As shown in FIG. 4, myomectomy screw retractor 10 is inserted such that tool assembly 20 is positioned over myoma 95. Articulating joint 26 of tool assembly 20 is actuated such that screw 22 defines angle θ relative to longitudinal axis "A-A" and is substantially aligned with the center of myoma 95. Angle θ is about 90°; however, angle θ can be in the range of about 0° to about 180° depending on the position of myoma 95 relative to myomectomy screw retractor 10.

Figure 5:
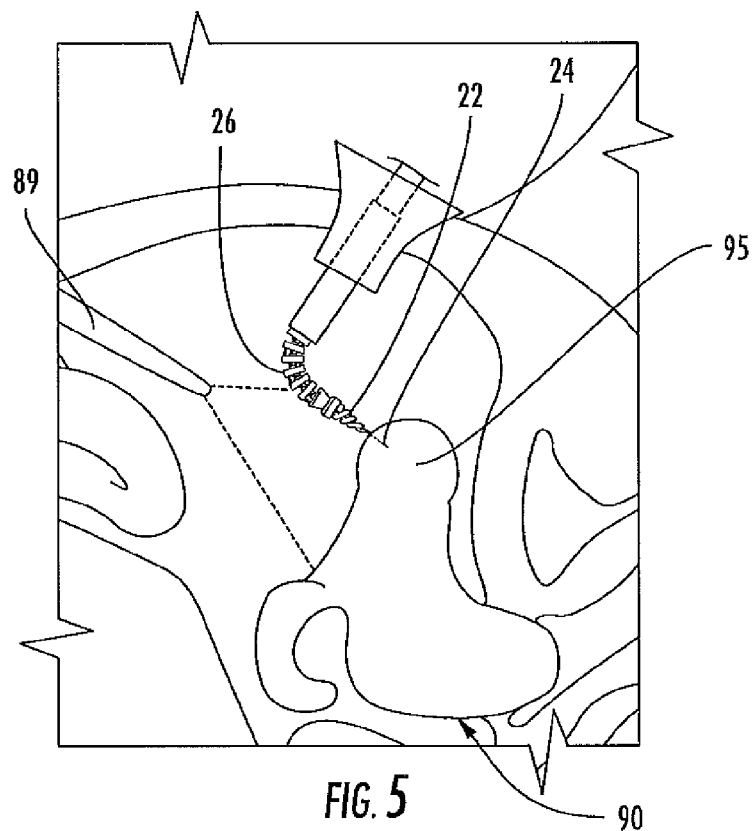
FIG. 5 is a perspective view of the myomectomy screw retractor of FIG. 3 with the guide wire of the myomectomy screw retractor extended into the myoma.

Referring to FIG. 5, Guide wire 24 is extended from the retracted position to the extended position such that guide wire 24 extends into myoma 95, substantially at the center of myoma 95. When guide wire 24 is extended into myoma 95, elongated body 14 is manipulated to engage myoma 95 with a distal end of screw 22. Guide wire 24 can be used to position screw 22 at the center of myoma 95. In embodiments, guide wire 24 provides a pilot hole for screw 22 in myoma 95.

Figure 6:
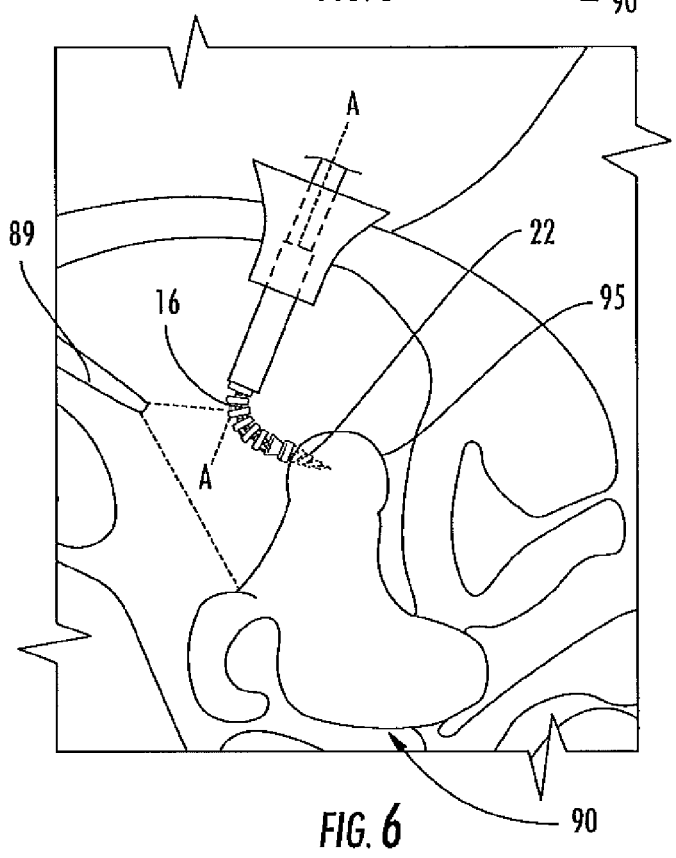
FIG. 6 is a perspective view of the myomectomy screw retractor of FIG. 3 with the screw of the myomectomy screw retractor engaged with the myoma.
Figure 7A:
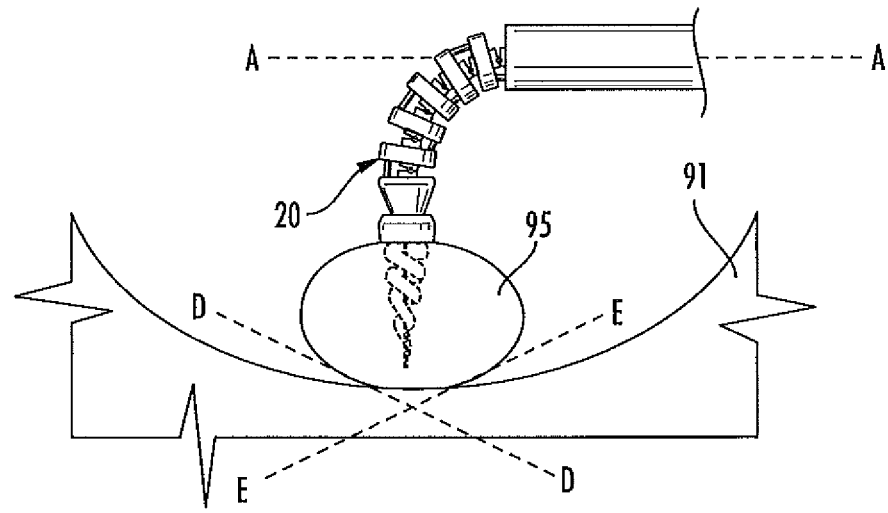
FIGS. 7A and 7B are side views illustrating the myomectomy screw retractor pitching the myoma backward.
Figure 7B:
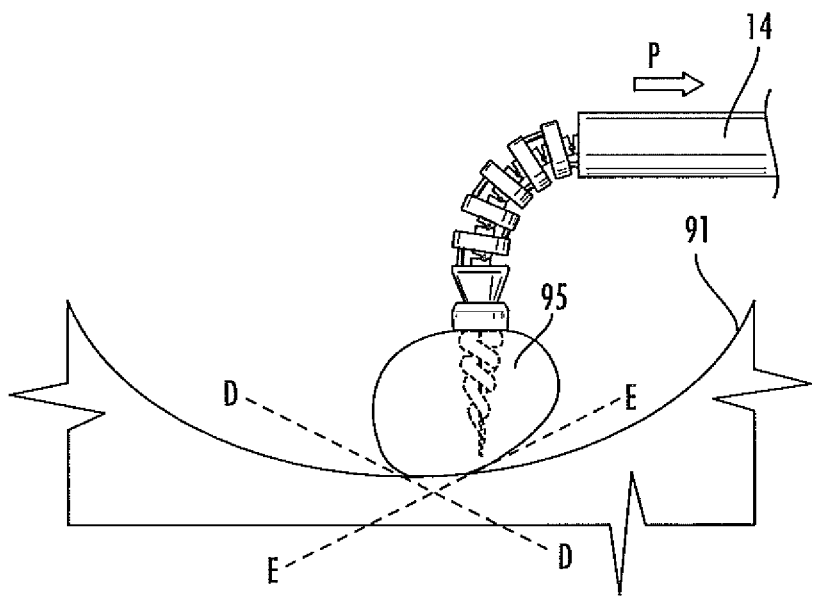

Referring to FIG. 6, screw 22 is coupled to rotatable shaft 16 and rotatable shaft 16 is rotated about longitudinal axis "A-A" which is operatively associated with screw 22 to turn screw 22 into myoma 95 until the proximal end of screw 22 is positioned substantially within myoma 95. It will be appreciated that in the case of a myoma that has a length less than the length of screw 22, the proximal end of screw 22 may not be disposed entirely within myoma 95, such that screw 22 can apply traction, pitch, and roll myoma 95. When screw 22 is positioned substantially within myoma 95, guide wire 24 is retracted from the extended position to the retracted position to withdraw guide wire 24 from myoma 95.

Referring to FIGS. 7A-9, when screw 22 is engaged with myoma 95, different cutting planes "D-D", "E-E", "F-F", and "G-G" can be exposed by pitching, rolling, and providing traction to myoma 95 by manipulation of elongated body 14. For example, cutting plane "D-D" is exposed by applying a force along arrow "P" inline with longitudinal axis "A-A" to pitch myoma 95 (FIG. 7B) to expose cutting plane "D-D".

Figure 8A:
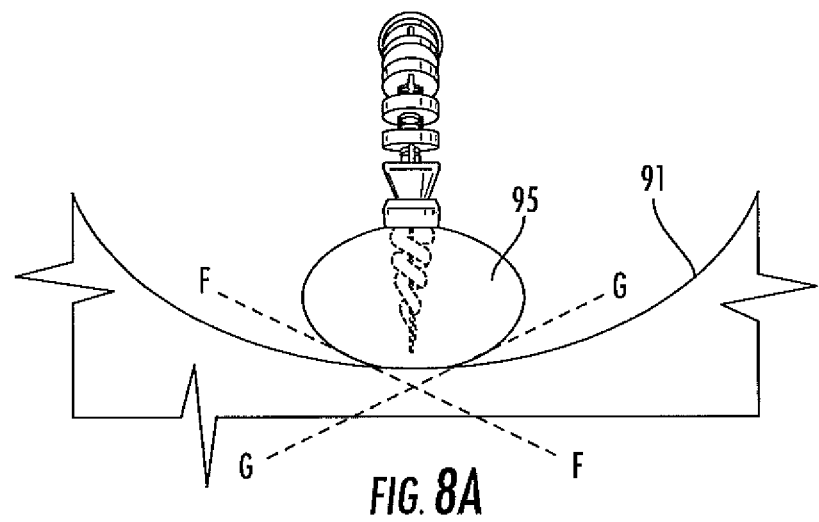
FIGS. 8A and 8B are front views illustrating the myomectomy screw retractor rolling the myoma.
Figure 8B:
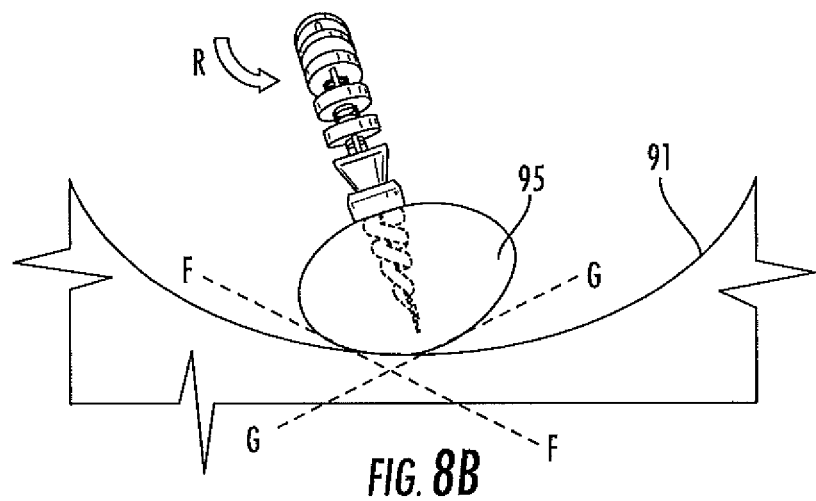

In another example, illustrated in FIGS. 8A and B, cutting plane "G-G" is exposed by applying an angular or radial force about longitudinal axis "A-A" to roll myoma 95, as represented by arrow "R". In yet another example, traction is applied by manipulating elongated body 14 to pull myoma 95 away from uterine wall 91, substantially perpendicular to longitudinal axis "A-A", as represented by arrow T in FIG. 9. In some embodiments, access device 82 is used as a fulcrum to apply traction to myoma 95.

It will be appreciated that as cutting planes "D-D", "E-E", "F-F", and "G-G" are exposed, a cutting instrument (not shown) is used to dissect myoma 95 from uterine wall 91 along cutting planes "D-D", "E-E", "F-F", and "G-G". Myoma 95 can be pitched and rolled multiple times allowing a clinician to progressively cut along each cutting plane "D-D", "E-E", "F-F", and "G-G" until myoma 95 is dissected from uterine wall 91. Uterine wall 91 is shown as an interior wall of uterus 90 in FIGS. 7A-8B and uterine wall 91 is shown as an exterior wall of uterus 90 in FIG. 9; however, pitching and rolling of myoma 95 can occur in a similar manner for either interior or exterior walls. In certain embodiments, locking mechanism 28 is extended into myoma 95 to retain myoma 95 in a fixed radial position about screw 22 before myoma 95 is pitched and rolled.

Figure 9:
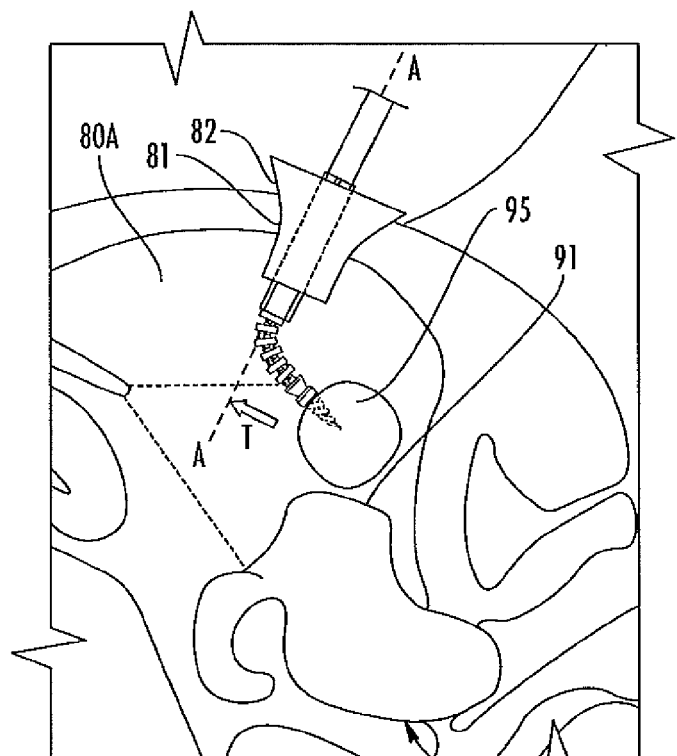
FIG. 9 is a perspective view of the myomectomy screw retractor of FIG. 3 with the myoma dissected from the uterus and engaged with the screw of the myomectomy screw retractor.
Figure 10:
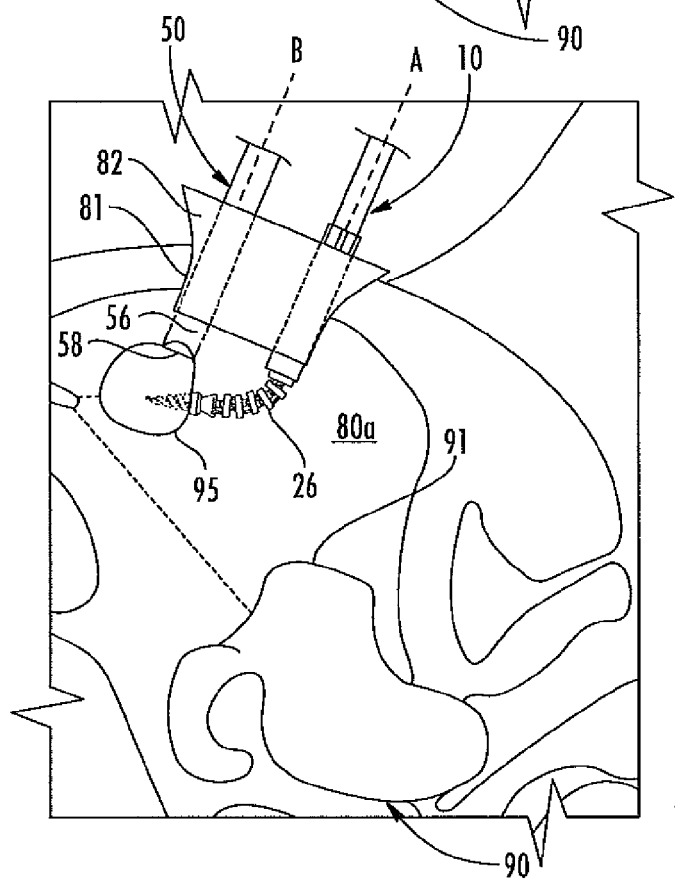
FIG. 10 is a perspective view of the myomectomy screw retractor of FIG. 3 with a morcellator inserted into the abdominal cavity and the myoma positioned at the distal end of the morcellator.

Referring now to FIGS. 9 and 10, when myoma 95 is dissected from uterine wall 91, morcellator 50 is inserted into body cavity 80a. In embodiments, morcellator 50 is inserted through access device 82 such that longitudinal axis "B-B" of morcellator 50 is orientated substantially parallel to longitudinal axis "A-A" of myomectomy screw retractor 10. In embodiments, morcellator 80 is inserted through a second incision 81a (FIG. 3). Articulating joint 26 is positioned such that screw 22 is substantially perpendicular to longitudinal axis "B-B" of morcellator 50. Sleeve 56 of morcellator 50 is positioned to engage an outer surface of myoma 95 such that the distal end of cutting tube 58 and sleeve 56 engage the outer surface of myoma 95 (FIG. 10).

A morcellator drive (not shown) is activated to rotate cutting tube 58 about longitudinal axis "B-B". As cutting tube 58 rotates, it draws strips of tissue from the outer surface of myoma 95 and through cutting tube 58 and expels the strips through the proximal end of morcellator 50.

In embodiments, screw 22 is decoupled from rotatable shaft 16 such that as cutting tube 58 draws tissue from the outer surface of myoma 95, screw 22 freely rotates about rotatable shaft 16 as myoma 95 rotates. In some embodiments, screw 22 remains coupled to rotatable shaft 16 such that screw 22 is actively rotated by rotatable shaft 16 to feed the outer surface of myoma 95 into cutting tube 58 of morcellator 50. In particular embodiments, motion detector 51 deactivates cutting tube 58 if the distal end of morcellator 50 is displaced while cutting tube 58 is activated. The deactivation of cutting tube 58 prevents cutting tube 58 from engaging tissue other than myoma 95 if the rotation of myoma 95 causes cutting tube 58 to be displaced. Cutting tube 58 engages myoma 95 until myoma 95 is fully morcellated and removed from the body cavity 80a through the proximal end of morcellator 50. Thereafter, morcellator 50 and myomectomy screw retractor 10 can be removed from port 82, port 82 can be removed from incision 81, and incision 81 can be closed.

Figure 11:
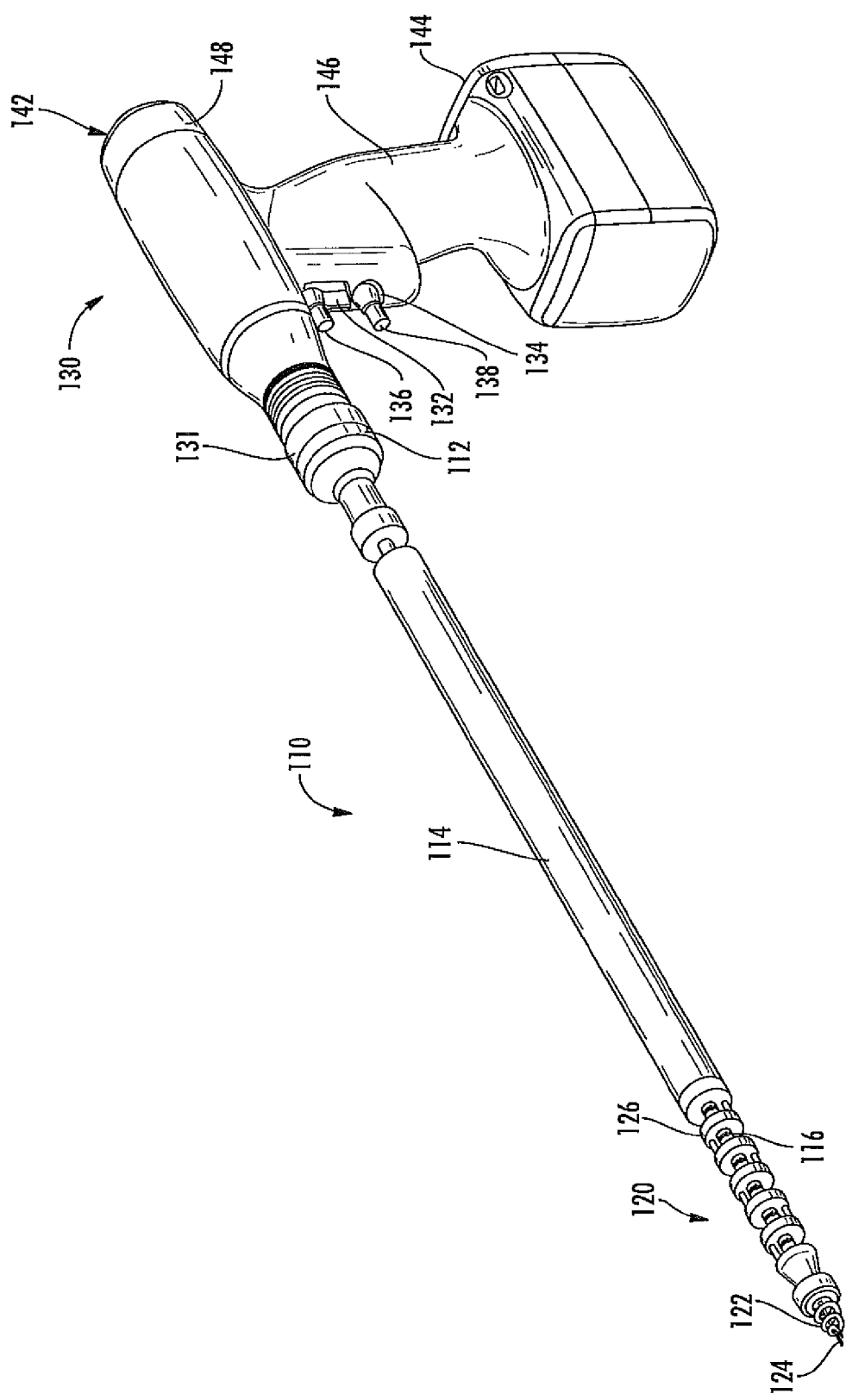
FIG. 11 is a perspective view of a myomectomy screw retractor end effector in accordance with the present disclosure coupled to a motorized handle assembly.

Referring to FIG. 11, another embodiment of a myomectomy screw retractor 110 is provided in accordance with the present disclosure. Myomectomy screw retractor 110 includes a proximal end 112, an elongated body 114, a rotatable shaft 116, and a tool assembly 120. The elongated body 114, rotatable shaft 116, and tool assembly 120 of myomectomy screw retractor 110 are substantially similar to elongated body 14, rotatable shaft 16, and tool assembly 20 of myomectomy screw retractor 10 described above with like elements represented by similar labels, as such only the differences will be described in detail below. Moreover, myomectomy screw retractor 110 interacts with morcellator 50 in a manner substantially similar to myomectomy screw retractor 10, as such only the differences will be described in detail below.

With continued reference to FIG. 11, proximal end 112 of myomectomy screw retractor 110 is selectively connected to an adaptor 131 of a powered instrument 130. Powered instrument 110 is configured to selectively connect to a plurality of different end effectors, via an adapter or shaft assembly 131 that is configured for actuation and manipulation by powered instrument 130. In particular, powered instrument 130 is configured for selective connection with shaft assembly 131, and, in turn, shaft assembly is configured for selective connection with any one of a plurality of different end effectors or tool assemblies. Other configurations are contemplated, such as, for example, an end effector attached to a shaft that is not removable, a remote power source and/or motor, and configurations including integral or remote computerized control.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire content of each of which being hereby incorporated herein by reference, for a detailed description of the construction and operation of exemplary powered instrument 130. Powered instrument 130 may include one or more motors powered by a battery, generator, or electrical power socket.

Figure 12:
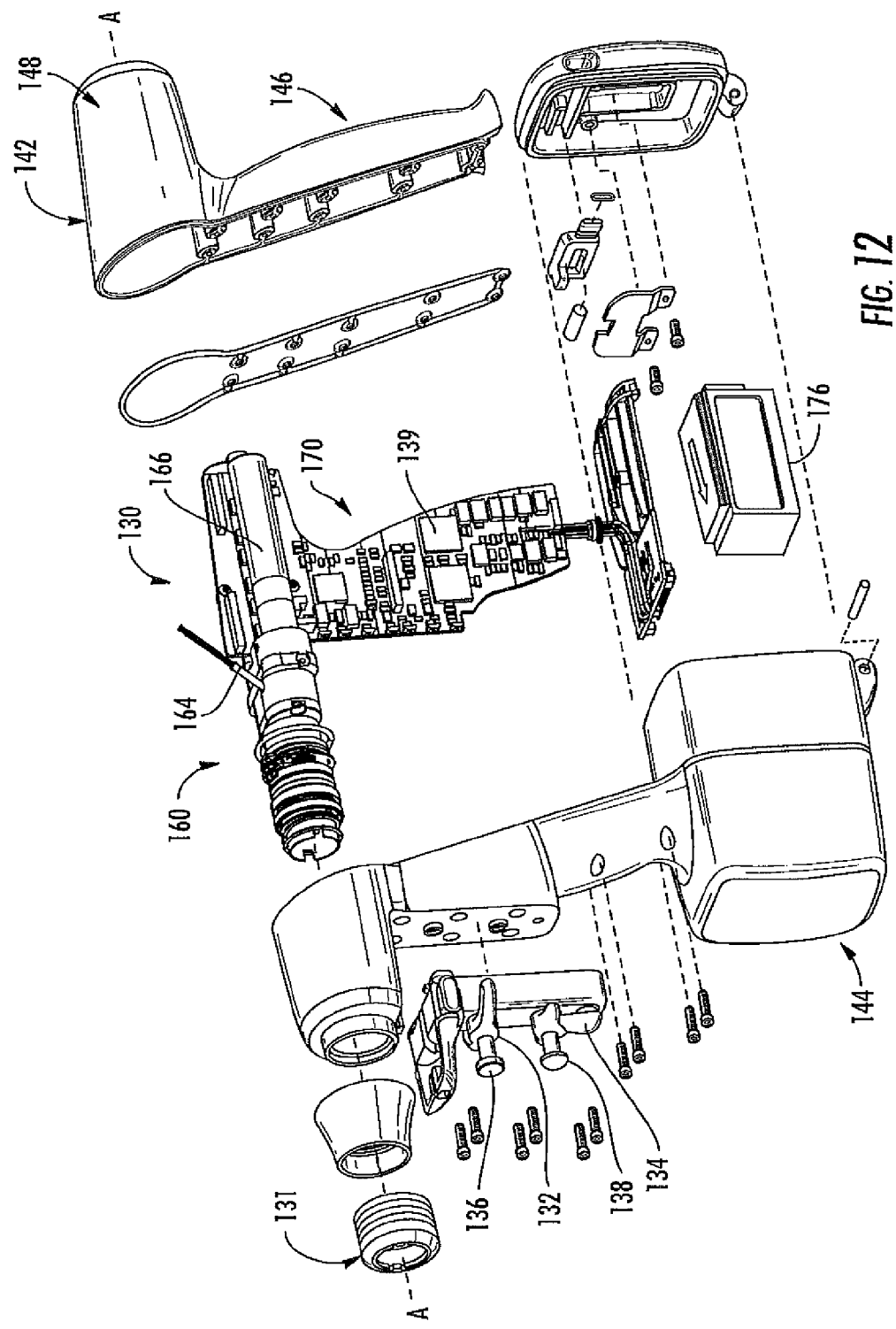
FIG. 12 is an exploded view showing the components of the motorized handle assembly of FIG. 11.

Generally, as illustrated in FIGS. 11 and 12, powered instrument 130 includes a handle housing 142 having a lower housing portion 144, an intermediate housing portion 146 extending from and/or supported on lower housing portion 144, and an upper housing portion 148 extending from and/or supported on intermediate housing portion 146. Handle housing 142 defines a cavity therein in which a circuit board or controller 170 and a drive mechanism 160 are situated. Drive mechanism 160 may include a first motor 164 used to select a rotatable drive member of powered instrument 130, and a second motor 166 used to drive each rotatable drive member of powered instrument 130.

Circuit board 170 is configured to control the various operations of powered instrument 130. In accordance with the present disclosure, handle housing 142 provides a housing in which a rechargeable battery 176 is removably situated. Battery 176 is configured to supply power to any of the electrical components of powered instrument 130. While a battery 176 is shown and contemplated, any known power source may be used, such as, for example a power cord or the like.

As illustrated in FIGS. 11 and 12, handle housing 142 supports a first rocker device 132, a second rocker device 134, a first control button 136, and a second control button 138. Each one of rocker devices 132, 134 and control buttons 136, 138 includes a respective magnet (not shown) that is moved by the actuation of an operator. Moreover, each one of rocker devices 132, 134 and control buttons 136, 138 can function in a binary manner, i.e., on or off, or in an analog manner.

Rocker devices 132, 134 and control buttons 136, 138 are programmable to manipulate to control tool assembly 120. Below is an example of how each of rocker devices 132, 134 and control buttons 136, 138 can be operatively associated with tool assembly 20.

First rocker device or first actuator 132 is operatively associated with an articulating joint 126 to control an articulation angle between tool assembly 120 and longitudinal axis, similar to the articulation angle θ and longitudinal axis "A-A" described in detail above with respect to articulating joint 26 and first actuator 32. Second rocker device or second actuator 134 is operatively associated with guide wire 124 to move guide wire 124 between a retracted position and an extended position, similar to guide wire 24 of myomectomy screw retractor 10 described in detail above.

First control button or rotation controller 136 is operatively associated with rotating shaft 116 to rotate rotating shaft 116, similar to rotatable handle 36 of myomectomy screw retractor 10 discussed above. First control button 136 can include a forward position, a reverse position, and/or a neutral position. When first control button 136 is in the forward position, rotating shaft 116 rotates in a clockwise direction to advance screw 122. When first control button 136 is in the reverse position, rotating shaft 116 rotates in a counter-clockwise direction to retract screw. When first control button 136 is in the neutral position, rotating shaft 116 is free rotate permitting screw 122 to cooperate with rotation induced by an external device, similar to screw 22 of myomectomy screw retractor 10 in the decoupled condition.

In embodiments, powered instrument 130 includes a screw synchronizer 139 operatively associated with rotating shaft 116 and morcellator 50 includes a morcellator synchronizer 53 in communication with screw synchronizer

139. Screw synchronizer 139 is configured to automatically control the rotation of rotating shaft 116 synchronizing the rotation of screw 122 with the rate at which cutting tube 58 of morecellator 50 draws tissue from the outer surface of myoma 95.

In some embodiments, when cutting tube 58 of morcellator 50 engages an outer surface of myoma 95, screw synchronizer 139 and morcellator synchronizer 53 communicate to synchronize the rotation of screw 122 with the activation of morcellator 50. When the rotation of screw 122 is synchronized to the activation of morcellator 50, screw 122 rotates myoma 95 to provide a constant feed of tissue to cutting tube 58.

Figure 13:
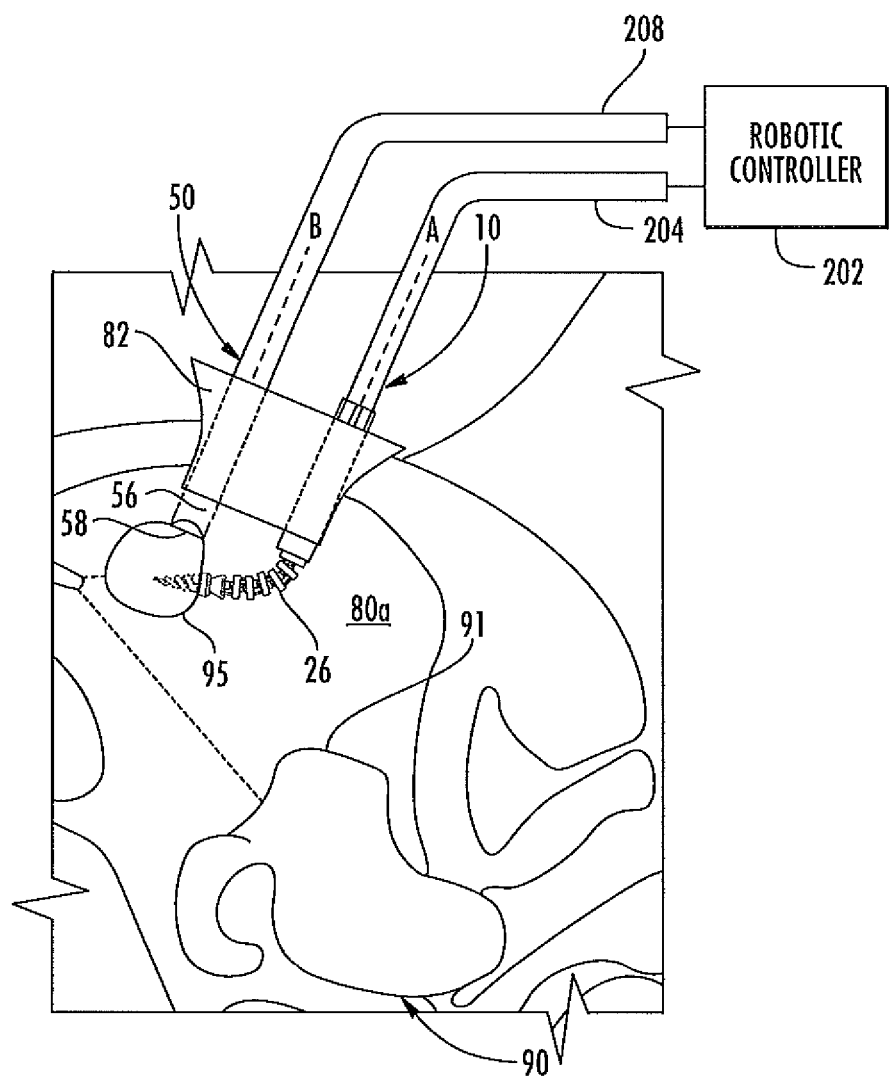
FIG. 13 is a perspective schematic view of end effectors of a robotic surgical system in accordance with the present disclosure inserted into the abdominal cavity of a patient.

Referring now to FIG. 13, various aspects disclosed herein may also be configured to work with a robotic surgical system 201 and what is commonly referred to as "Telesurgery". Robotic surgical system 201 employs various robotic elements to assist the surgeon in the operating theatre and allow remote operation (or partial remote operation) of surgical instrumentation. Robotic arms 204, 206, gears, cams, pulleys, electric and mechanical motors, etc. may be employed for this purpose and may be designed with robotic surgical system 201 to assist the surgeon during the course of an operation or treatment. Robotic surgical system 201 may include a robotic system controller 202 having remotely steerable systems, automatically flexible surgical systems, remotely flexible surgical systems, remotely articulating surgical systems, wireless surgical systems, modular or selectively configurable remotely operated surgical systems, etc.

Robotic system controller 202 may be employed with one or more consoles that are next to the operating theater or located in a remote location. In this instance, one team of clinicians may prep the patient for surgery and robotic surgical system 201 with one or more of the instruments disclosed herein, e.g., myomectomy screw retractor 110 and morcellator 50, while another clinician (or group of clinicians) remotely control the instruments via robotic system controller 202. As can be appreciated, a highly skilled clinician may perform multiple operations in multiple locations without leaving his/her remote console which can be both economically advantageous and a benefit to the patient or a series of patients.

Robotic arms 204, 206 of robotic surgical system 201 are typically operatively coupled to a pair of master handles by a controller. The handles can be moved by the clinician to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller, or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

According to aspects of the present disclosure, a surgical kit is provided incorporating a myomectomy screw retractor and a morcellator, both sealed in sterile packaging. In embodiments, the myomectomy screw retractor and the morecellator are end effectors configured to attach to a powered instrument and/or a robotic surgical system.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. A myomectomy screw retractor comprising:
   an elongated body defining a longitudinal axis;
   a tool assembly disposed at a distal portion of the elongated body, the tool assembly including:
      a screw;
      a rotating shaft extending proximally from the screw through the elongated body, the rotating shaft selectively coupled to the screw; and
      an articulating joint interconnecting the elongated body and the screw and articulatable to move the tool assembly between a linear condition and an articulated condition, the screw disposed along the longitudinal axis when the tool assembly is in the linear condition and the screw defining an angle with respect to the longitudinal axis when the tool assembly is in the articulated condition; and
   a screw synchronizer configured to control rotation of the rotating shaft and to communicate with a morcellator such that rotation of the rotating shaft is synchronized with a function of the morcellator.

2. The myomectomy screw retractor of claim 1, wherein the tool assembly of the myomectomy screw retractor includes a guide wire coaxially disposed within the screw, a distal end of the guide wire positioned proximal to a distal end of the screw when the guide wire is in a retracted position and the distal end of the guide wire extended distally beyond the distal end of the screw when the guide wire is in an extended position.

3. The myomectomy screw retractor of claim 2, wherein the guide wire is removable through a proximal end of the elongated body.

4. The myomectomy screw retractor of claim 1, wherein the tool assembly includes a locking mechanism extendable about the outer surface of the screw, the locking mechanism configured to engage tissue engaged by the screw to inhibit rotation of tissue relative to the screw.

5. The myomectomy screw retractor of claim 1, wherein a proximal portion of the elongated body includes an adaptor, the adaptor including an interface for manipulating the tool assembly.

6. A surgical system comprising:
   a myomectomy screw retractor, comprising:
      an elongated body defining a longitudinal axis; and
      a tool assembly disposed at a distal portion of the elongated body, the tool assembly including:
         a screw;
         a rotating shaft extending proximally from the screw through the elongated body, the rotating shaft selectively coupled to the screw;

an articulating joint interconnecting the elongated body and the screw and articulatable to move the tool assembly between a linear condition and an articulated condition, the screw disposed along the longitudinal axis when the tool assembly is in the linear condition and the screw defining an angle with respect to the longitudinal axis when the tool assembly is in the articulated condition; and a screw synchronizer configured to control rotation of the rotating shaft and a morcellator comprising:

an elongated tube having a sleeve at the distal portion of the elongated tube and defining a second longitudinal axis;

a cutting tube disposed within the sleeve, the cutting tube activateable to rotate about the second longitudinal axis, a distal end of the cutting tube positioned adjacent a distal end of the sleeve; and a morcellator synchronizer operatively associated with the cutting tube, the screw synchronizer in communication with the morcellator synchronizer to rotate the screw in cooperation with the rotation of the cutting tube.

7. The surgical system of claim 6, wherein the morcellator includes a motion detector positioned within the distal portion of the elongated tube, the motion detector configured to deactivate the cutting tube when the distal portion of the elongated tube is displaced while the cutting tube is rotating.

8. The surgical system of claim 6, wherein at least one of the myomectomy screw retractor and the morcellator is an end effector configured to couple to a powered surgical instrument.

9. The surgical system of claim 6, wherein at least one of the myomectomy screw retractor and the morcellator is an end effector configured to couple to a robotic surgical system.

* * * * *